(12) United States Patent
Mulvaney

(10) Patent No.: US 6,779,739 B2
(45) Date of Patent: Aug. 24, 2004

(54) WATER DISPLAY SYSTEM WITH GERMICIDAL LIGHT SOURCE

(75) Inventor: Patrick T. Mulvaney, Glen Allen, VA (US)

(73) Assignee: Hamilton Beach/Proctor-Silex, Inc., Glen Allen, VA (US)

( * ) Notice: Subject to any disclaimer, the term of this patent is extended or adjusted under 35 U.S.C. 154(b) by 178 days.

(21) Appl. No.: 10/108,520

(22) Filed: Mar. 28, 2002

(65) Prior Publication Data

US 2002/0139865 A1 Oct. 3, 2002

Related U.S. Application Data

(60) Provisional application No. 60/280,164, filed on Mar. 30, 2001.

(51) Int. Cl.[7] .............................................. B05B 17/08
(52) U.S. Cl. ............................ 239/17; 239/17; 239/18; 239/20; 239/23; 210/748
(58) Field of Search ............................ 239/18, 17, 20, 239/23, 211, 193, 194; 210/748

(56) References Cited

U.S. PATENT DOCUMENTS

| 2,265,252 A | 12/1941 | Schaefer |
| 2,638,644 A | 5/1953 | Rauhut |
| 3,812,370 A | 5/1974 | LaViolette |
| 4,362,090 A | 12/1982 | Whiteley |
| 4,630,475 A | 12/1986 | Mizoguchi |
| 4,899,057 A | 2/1990 | Koji |
| 4,940,885 A | 7/1990 | Challenger |
| 5,114,576 A | * 5/1992 | Ditzler et al. ............ 210/195.1 |
| 5,215,657 A | 6/1993 | Goldfield et al. |
| 5,217,696 A | 6/1993 | Wolverton et al. |
| 5,348,623 A | 9/1994 | Salmon |
| 5,433,923 A | 7/1995 | Wolverton et al. |
| 5,571,409 A | * 11/1996 | Scarborough ................ 239/20 |
| 5,589,132 A | 12/1996 | Zippel |
| 5,677,982 A | 10/1997 | Levine et al. |
| 5,859,952 A | 1/1999 | Levine et al. |
| 6,042,720 A | 3/2000 | Reber et al. |
| 6,098,963 A | 8/2000 | Dubin et al. |
| 6,117,219 A | 9/2000 | Muhr |
| 6,464,884 B1 | * 10/2002 | Gadgil ....................... 210/748 |

FOREIGN PATENT DOCUMENTS

| EP | 0 446 011 A1 | 11/1991 |
| EP | 0 446 011 B1 | 11/1991 |

* cited by examiner

Primary Examiner—Steven J. Ganey
(74) Attorney, Agent, or Firm—Akin Gump Strauss Hauer & Feld, LLP

(57) ABSTRACT

An odor-reducing water display system includes a reservoir, a pump for removing water from the reservoir, a conduit in fluid communication with the pump for returning the removed water to the reservoir, and a germicidal light source positioned for directing radiant energy toward the water to thereby reduce microbes and their accompanying odor that may be present in the water.

22 Claims, 5 Drawing Sheets

WATER DISPLAY SYSTEM WITH GERMICIDAL LIGHT SOURCE

CROSS-REFERENCE TO RELATED APPLICATIONS

This application claims the benefit of U.S. Provisional Application No. 60/280,164 filed on Mar. 30, 2001, and entitled "Fountain Including Ultraviolet Light," the disclosure of which is hereby incorporated by reference.

BACKGROUND OF THE INVENTION

This invention relates to water display systems for providing a pleasant visual and/or audible experience to observers, and more particularly to a water display system with a germicidal light source for removing odors and/or contaminants from water or other liquids that may be circulated through the water display system.

Water display systems, such as water fountains, waterfalls or the like, have long been used in gardens and similar outdoor locations, as well as in indoor locations on a typically much smaller scale. As shown in FIG. 1, a conventional water display system 2 includes a reservoir 4 for holding a quantity of water 6, a pump 8 located within the reservoir in fluid communication with the water 6, and a conduit 10 with an inlet end 12 in fluid communication with the pump 8 and an outlet end 14 that is positioned above an upper surface 16 of the water 6 in the reservoir. In use, the pump 8 draws in water 6 from the reservoir 4, forces it up through the conduit 12 and out through the outlet end 14 where it falls back into the reservoir 4, as represented by arrows 18, to be recycled again through the pump and conduit. More complex versions of fountains may circulate the reservoir water through several pools or terraces located at different heights to produce both visually and audibly pleasing effects. During circulation of the water, however, it may be aerated and thus come in contact with airborne contaminants, such as mold spores, bacteria, viruses and/or other microbes. Over time, these microbes may affect the water quality and/or create unpleasant odors. Although these microbes may be controlled through application of chemicals to the water in the reservoir, such as chlorine or other anti-microbial solutions, the chemicals themselves may produce unpleasant odors.

Accordingly, it would be desirable to provide a system and method of improving the water quality in water display systems, while reducing or eliminating the need for chemicals and their consequent odor generation.

BRIEF SUMMARY OF THE INVENTION

According to one aspect of the invention, a liquid display system comprises a reservoir for holding a quantity of liquid therein, a conduit having an inlet end positioned for receiving liquid from the reservoir and an outlet end positioned for returning liquid to the reservoir above a level of the liquid in the reservoir, a pump in fluid communication with the reservoir and the inlet end of the conduit for forcing liquid from the reservoir through the conduit and out of the outlet end, and a germicidal light source positioned for directing radiant energy toward the liquid. In this manner, microbes or other contaminants and their associated odors can be substantially reduced or eliminated.

According to a further aspect of the invention, an odor-reducing water display system includes a reservoir for holding a quantity of water, a pump in fluid communication with the reservoir for removing water therefrom, and a conduit in fluid communication with the pump. The conduit has an outlet end that is positioned above a level of water in the reservoir to thereby return the removed water to the reservoir, such that water returning to the reservoir is at least partially aerated and exposable to microbes. The odor-reducing water display system further includes a germicidal light source that is positioned for directing radiant energy toward the water to thereby reduce microbes and their accompanying odor that may be present in the water.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings.

The invention will now be described in greater detail with reference to the drawings, wherein like parts throughout the drawing figures are represented by like numerals.

DETAILED DESCRIPTION OF THE INVENTION

Figure 1:
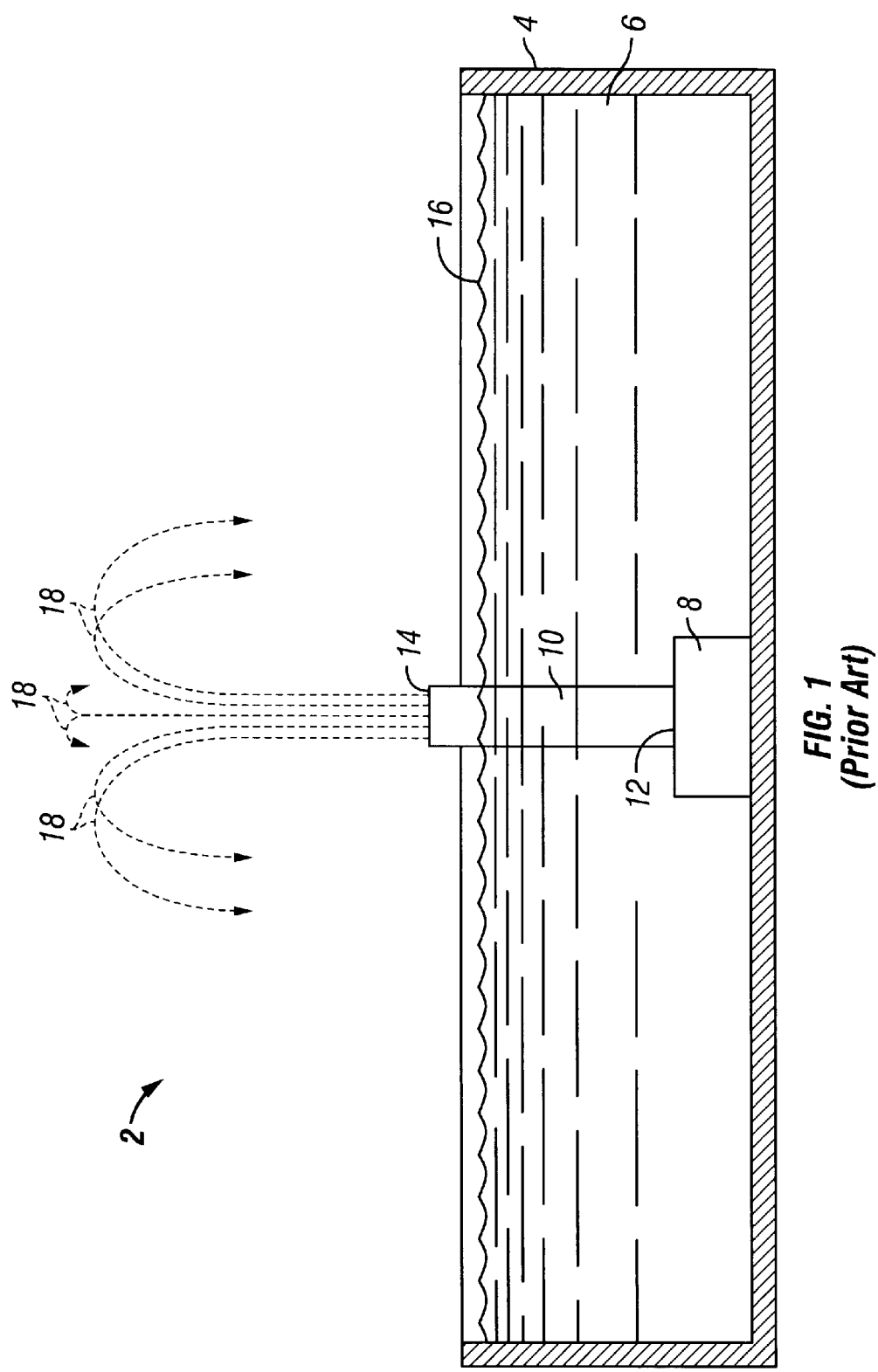
FIG. 1 is a cross sectional schematic view of a prior art water fountain.
Figure 2:
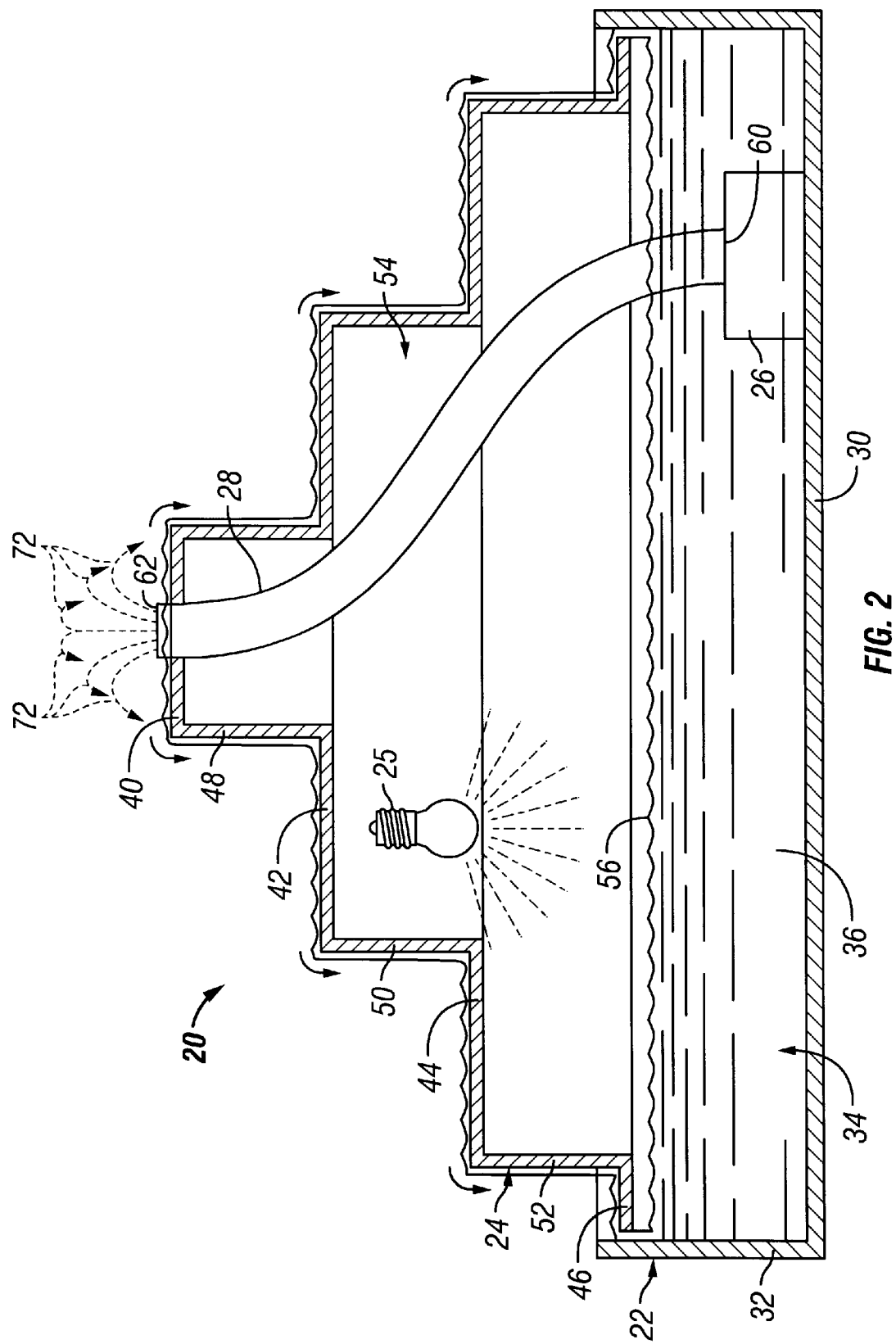
FIG. 2 is a cross sectional schematic view of a water display system according to one embodiment of the present invention.

Referring now to the drawings, and to FIG. 2 in particular, a water display system 20 in accordance with one embodiment of the present invention is illustrated. The water display system 20, shown here as a water fountain, includes a reservoir 22, a hollow body portion 24 positioned above the reservoir 22, a pump 26 positioned in the reservoir, a conduit 28 extending between the pump 26 and an upper end of the hollow body portion 24 for delivering water or other liquid from the reservoir to the exterior of the hollow body portion to thereby create pleasing audible and visual effects, and a germicidal light source 25 that is positioned for directing radiant energy toward the liquid in the reservoir 22.

The reservoir 22 includes a bottom wall 30 and a continuous side wall 32 that extends generally upwardly from the bottom wall to thereby form a hollow interior 34 into which a volume of water or other liquid 36 can be received and held. Preferably, the reservoir 22 is of sufficient size to also contain the pump 26.

The hollow body portion 24 preferably includes terraces or pools 40, 42, 44 and 46 that are oriented generally horizontally, a riser 48 that extends between the terraces 40 and 42, a riser 50 that extends between the terraces 42 and 44, and a riser 52 that extends between the terraces 44 and 46 to thereby form a hollow interior 54.

The pump 26 is preferably of the submersible type for mounting to the bottom wall 30 of the reservoir 22 below a level 56 of liquid within the hollow interior 34, but may alternatively be mounted to the hollow body portion 24 or at other locations remote from the reservoir 22, as will be described in greater detail below with respect to further embodiments of the invention. The pump 26 is preferably a submersible pump for moving water from the reservoir 22 up through the conduit 28 at a predetermined flow rate and height. For relatively small tabletop fountains or displays, the pump 26 is preferably of small profile and, by way of example, may be of the piston, diaphragm, or centrifugal type. A power source (not shown), such as line power or one or more batteries, is connectable to the pump 26 for operation thereof.

The conduit 28 includes an inlet end 60 that is in fluid communication with an outlet (not shown) of the pump 26 and an outlet end 62 that preferably extends through the uppermost terrace 40. The conduit 28 may be rigid or flexible, and constructed of a variety of materials. For smaller tabletop fountains, the conduit can be constructed of a flexible, food grade plastic tubing material, such as food grade polyethylene, PVC, polypropylene or the like, so that plasticizers or other odor-emitting substances within the material are not transferred from the tubing to the water or other liquid passing therethrough. Although not shown, a nozzle may be installed at the outlet end 62 of the conduit 28 to define a particular spray pattern for the liquid exiting the conduit. Although a single conduit 28 is shown, it will be understood that more than one conduit can be provided, depending on the particular fountain configuration and the particular effect desired.

The germicidal light source 25 is of well-known construction and is preferably positioned within the hollow interior 54 of the hollow body portion 24 and is arranged to project radiant energy toward the liquid 36 in the reservoir 22. Preferably, the light source projects radiant energy in the ultraviolet region of the electromagnetic spectrum at a wavelength of approximately 254 nm in order to eliminate microbes and their odors that may be present in the liquid. With this arrangement, the germicidal light source 25, together with the hollow body portion 24 and the reservoir 22, function as an irradiation chamber for exposing liquid in the reservoir to the ultraviolet light.

During operation of the water display system 20, water or other liquid 36 within the reservoir 22 is drawn into the pump 26 and forced through the conduit 28 and out the outlet end 62 to form a spout, as represented by arrows 72, of a predetermined height and width. As the liquid falls toward the hollow body portion 24 and flows over the terraces and risers toward the reservoir 22, aeration of the liquid may occur. Microbes that come in contact with the liquid are brought into the reservoir 22 for exposure to the germicidal light source 25. In this manner, the microbes are substantially reduced or eliminated to thereby improve the water quality, and thus the odor, of the liquid. Accordingly, the liquid can be circulated throughout the system 20 for a greater number of cycles before being changed while substantially reducing or eliminating malodorous effects over prior art fountains.

Figure 3:
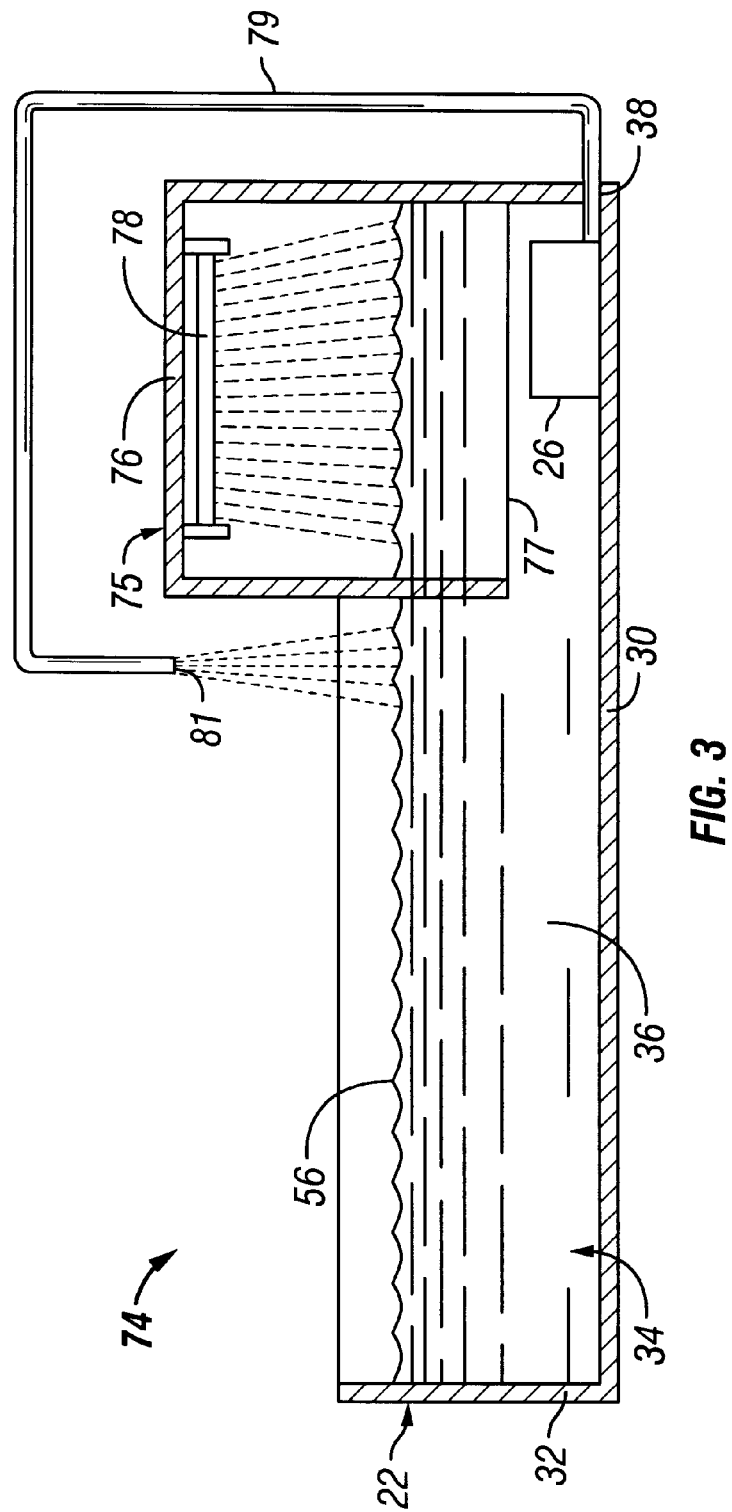
FIG. 3 is a cross sectional schematic view of a water display system according to a further embodiment of the present invention.

In configurations where it is desirous to construct a water display system without the hollow body portion 24, or where it is desirous to provide an irradiation chamber separate from the hollow body portion, a water display system 74 in accordance with a further embodiment of the invention is illustrated in FIG. 3, wherein like parts in the previous embodiment are represented by like numerals. The water display system 74 is similar to the water display system 20 previously described, with the exception that the hollow body portion 24 is not shown, although it may be provided, and an irradiation chamber 75 is positioned in the reservoir 22.

The irradiation chamber 75 includes a housing 76 that, as shown, is integrally formed with the reservoir 22, and a germicidal light source 78 positioned in the housing for projecting ultraviolet light toward liquid 36 within the housing 76 and the reservoir 22. A lower opening 77 is provided in the housing for admitting liquid from the reservoir. One or more vent holes (not shown) may also be provided in the housing so that the level of liquid in the housing is approximately the same as the level 56 of liquid in the reservoir 22. It will be understood that the irradiation chamber 75 need not be integrally formed with the reservoir 22, but may be separately formed and positioned for projecting ultraviolet light into the reservoir.

A conduit 79 extends from the submersible pump 26, through an opening 38 in the wall 32, and terminates at an outlet end 81 above the reservoir. The conduit 79 can be of any desired shape and configuration, and is only limited by the particular configuration of the water display system 74. A nozzle (not shown) may be installed at the outlet end 81 of the conduit 79 to define a particular spray pattern for the liquid exiting the conduit. Although a single conduit 79 is shown, it will be understood that more than one conduit can be provided, depending on the particular fountain configuration and effect desired. Although not shown, the conduit 79 can be positioned for discharging liquid onto a variety of different objects and/or surfaces, depending on the desired effect.

Figure 4:
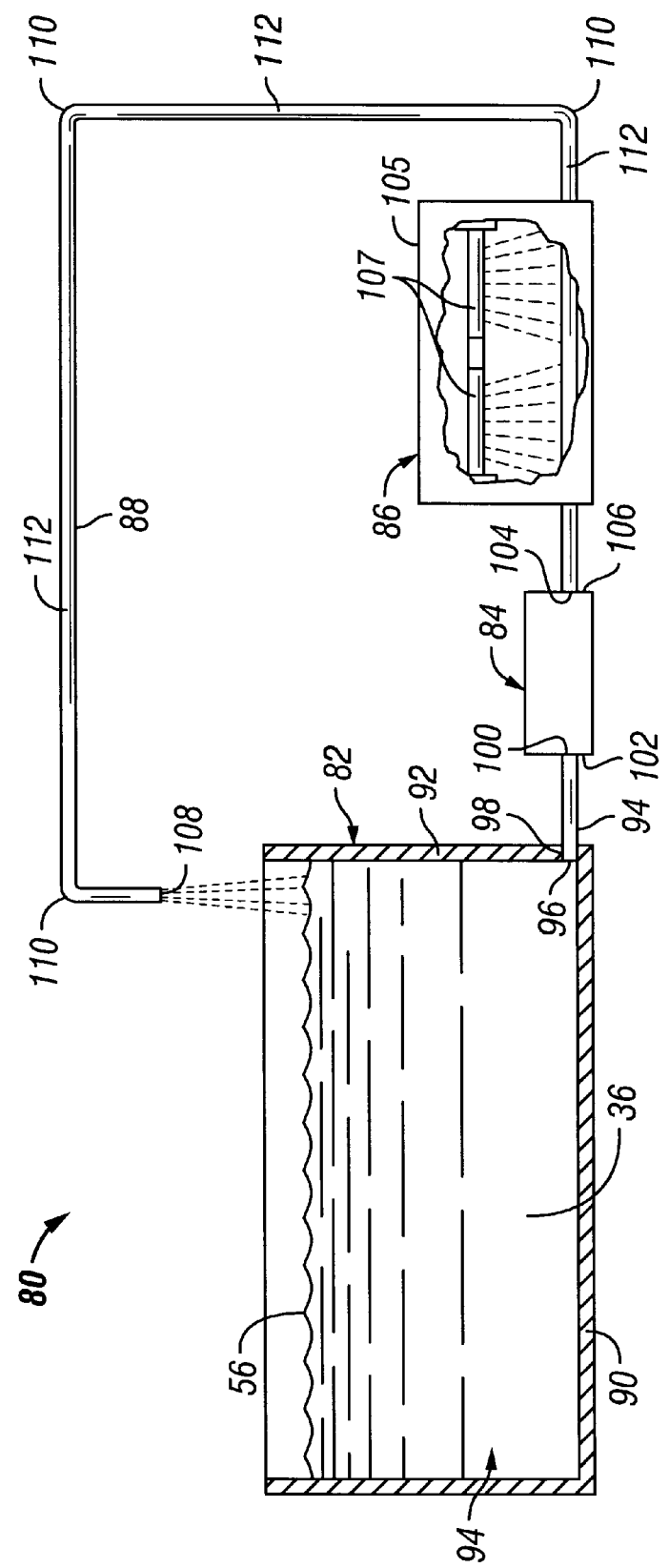
FIG. 4 is a cross sectional schematic view of a water display system according to an even further embodiment of the present invention.

With reference now to FIG. 4, a water display system 80 in accordance with a further embodiment of the invention is illustrated. The water display system 80 includes a reservoir 82, a pump 84 fluidly connected to the reservoir 82, an irradiation chamber 86 located downstream of and fluidly connected to the pump 84, and a conduit 88 extending between the irradiation chamber 86 and the reservoir 82.

The reservoir 82 includes a bottom wall 90 and a continuous side wall 92 that extends generally upwardly from the bottom wall to thereby form a hollow interior 94 into which a volume of water or other liquid 36 can be received and held. A tubular member or conduit 94 has an inlet end 96 that extends through an opening 98 in the side wall 92 and an outlet end 100 that is in fluid communication with an inlet 102 of the pump 84 so that fluid from the reservoir 82 can be delivered to the pump. In an alternative embodiment, the tubular member 94 can be eliminated and the pump 84 connected directly to the reservoir 82.

The pump 84 is preferably located outside of the reservoir 82, and therefore is of the non-submersible type. As in the previous embodiment, the pump is chosen to deliver fluid from the reservoir 82 at a predetermined flow rate and height.

The irradiation chamber 86 includes an elongate housing 105 with germicidal light sources 107 arranged longitudinally therein. As in the previous embodiment, the germicidal light sources 107 preferably emit radiant energy in the ultraviolet region at a wavelength of approximately 254 nm.

The conduit 88 preferably has an inlet end 104 that is in fluid communication with an outlet 106 the pump 84, and an outlet end 108 that is positioned for discharging liquid 36 back into the reservoir 82. The conduit 88 may have any number of turns 110 and/or segments 112, with one segment extending through the irradiation chamber 86. The conduit 88 is preferably constructed of an ultraviolet transparent or translucent material, especially the portion extending through the irradiation chamber 86, so that liquid traveling through the conduit 88 within the irradiation chamber 86 is exposed to radiant energy from the germicidal light source 107 transmitted through the conduit 88 to thereby substantially reduce or eliminate microbes that may be present in the liquid. As in the previous embodiment, the conduits 88 and 94 can be constructed of a flexible or rigid plastic tubing material, such as food grade polyethylene, PVC, polypropylene or the like, so that plasticizers or other odor-emitting substances within the material are not transferred from the tubing to the liquid passing therethrough.

A nozzle (not shown) may be installed at the outlet end 108 of the conduit 88 to define a particular spray pattern for the liquid exiting the conduit. Although a single conduit 88 is shown, it will be understood that more than one conduit can be provided, depending on the particular fountain configuration and effect desired. Moreover, although a hollow body portion is not shown in this embodiment, hollow or solid body portions of various configurations can be used for increased visual and audible effects.

Figure 5:
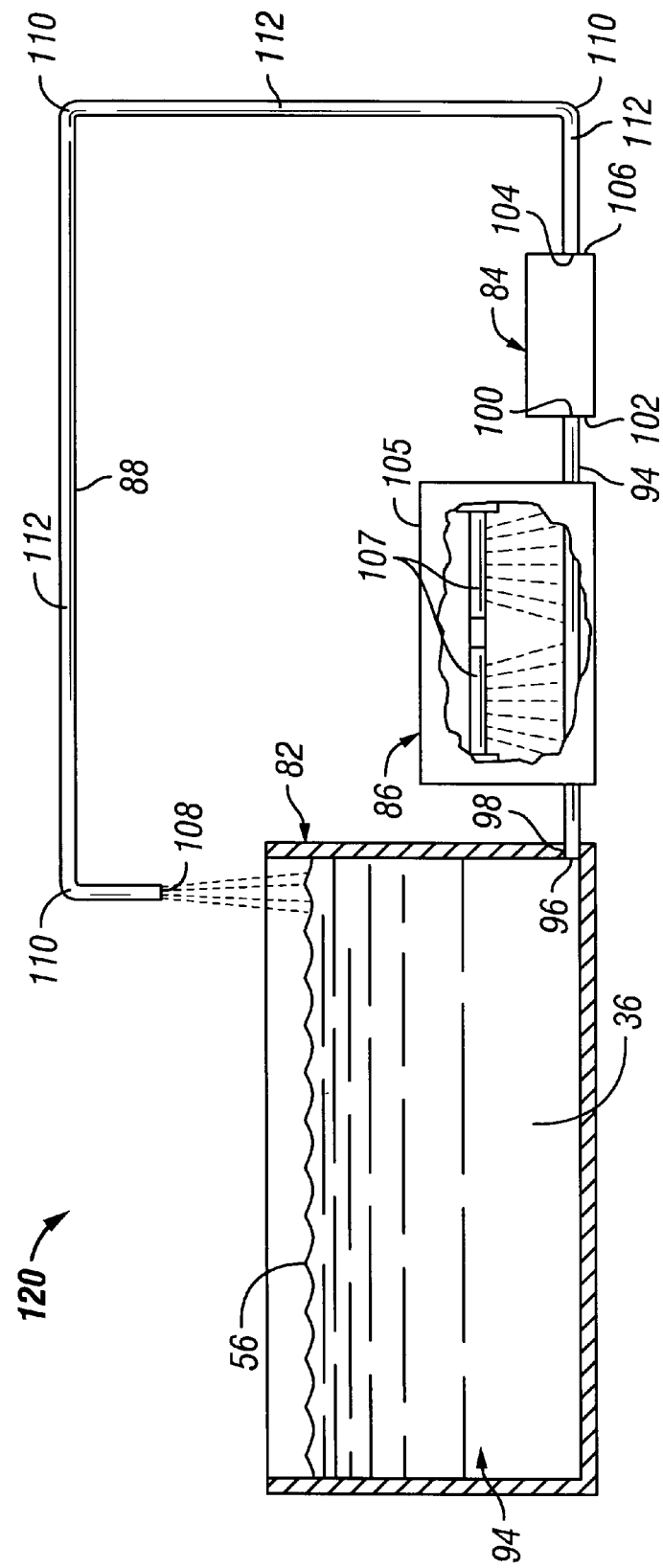
FIG. 5 is a cross sectional schematic view of a water display system according to yet another embodiment of the present invention.

With reference now to FIG. 5, a water display system 120 in accordance with a further embodiment of the invention is illustrated, wherein like parts in the previous embodiment are represented by like numerals. The water display system 120 is similar in construction to the water display system 80, with the exception that the pump 84 is positioned downstream of the irradiation chamber 86, with the tubular member or conduit 94 extending from the reservoir 82, through the irradiation chamber 86, and to the inlet end 102 of the pump 84. The tubular member 94 is preferably constructed of an ultraviolet transparent or translucent material so that liquid flowing therethrough is exposed to the radiant energy from the germicidal light source 107. With this arrangement, microbes that may be present in the liquid are substantially reduced or eliminated before reaching the pump 84.

It will be appreciated by those skilled in the art that changes could be made to the embodiments described above without departing from the broad inventive concept thereof. It will be understood, therefore, that this invention is not limited to the particular embodiments disclosed, but it is intended to cover modifications within the spirit and scope of the present invention as defined by the appended claims.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A liquid display system, comprising:
   a reservoir for holding a quantity of liquid therein;
   a conduit having an inlet end positioned for receiving liquid from the reservoir and an outlet end positioned for returning liquid to the reservoir above a level of the liquid in the reservoir;
   a pump in fluid communication with the reservoir and the conduit for forcing liquid from the reservoir through the conduit and out of the outlet end; and
   a germicidal light source positioned for directing radiant energy toward the liquid.

2. A liquid display system according to claim 1, and further comprising a hollow body portion situated above the reservoir, the outlet end of the conduit being positioned for discharging the liquid onto the hollow body portion.

3. A liquid display system according to claim 2, wherein the hollow body portion has an upper terrace and the outlet end of the conduit extends through the upper terrace.

4. A liquid display system according to claim 1, wherein the pump is a submersible pump and is positioned in the reservoir for contacting the liquid.

5. A liquid display system, comprising:
   a reservoir for holding a quantity of liquid therein;
   a conduit having an inlet end positioned for receiving liquid from the reservoir and an outlet end positioned for returning liquid to the reservoir above a level of the liquid in the reservoir;
   a pump in fluid communication with the reservoir and the conduit for forcing liquid from the reservoir through the conduit and out of the outlet end;
   a germicidal light source positioned for directing radiant energy toward the liquid; and
   a hollow body portion situated above the reservoir, the outlet end of the conduit being positioned for discharging the liquid onto the hollow body portion and the germicidal light source being located in the hollow body portion.

6. A liquid display system comprising:
   a reservoir for holding a quantity of liquid therein;
   a conduit having an inlet end positioned for receiving liquid from the reservoir and an outlet end positioned for returning liquid to the reservoir above a level of the liquid in the reservoir;
   a pump in fluid communication with the reservoir and the conduit for forcing liquid from the reservoir through the conduit and out of the outlet end;
   an irradiation chamber having a housing; and
   a germicidal light source located within the housing and being positioned for directing radiant energy toward the liquid.

7. A liquid display system according to claim 6, wherein the irradiation chamber is located in the reservoir.

8. A liquid display system according to claim 7, wherein the housing is integrally formed with the reservoir.

9. A liquid display system according to claim 6, wherein the irradiation chamber is located outside of the reservoir.

10. A liquid display system according to claim 9, wherein a portion of the conduit extends through the housing of the irradiation chamber.

11. A liquid display system according to claim 10, wherein at least the conduit portion is constructed of one of an ultraviolet transparent and translucent material such that radiant energy from the germicidal light source is transmitted to the liquid through the conduit portion.

12. A liquid display system according to claim 11, wherein the pump is positioned downstream of the irradiation chamber.

13. A liquid display system according to claim 11, wherein the pump is positioned upstream of the irradiation chamber.

14. An odor-reducing water display system, comprising:
   a reservoir for holding a quantity of water therein;
   a pump in fluid communication with the reservoir for removing water therefrom;
   a conduit in fluid communication with the pump, the conduit having an outlet end that is positioned above a level of water in the reservoir to thereby return the removed water to the reservoir, such that water returning to the reservoir is at least partially aerated and exposable to microbes; and a germicidal light source positioned for directing radiant energy toward the water to thereby reduce microbes and their accompanying odor that may be present in the water.

15. An odor-reducing water display system, comprising:

a reservoir for holding a quantity of water therein;

a pump in fluid communication with the reservoir for removing water therefrom:

a conduit in fluid communication with the pump, the conduit having an outlet end that is positioned above a level of water in the reservoir to thereby return the removed water to the reservoir, such that water returning to the reservoir is at least partially aerated and exposable to microbes;

an irradiation chamber having a housing; and a germicidal light source located within the housing and being positioned for directing radiant energy toward the water to thereby reduce microbes and their accompanying odor that may be present in the water.

16. An odor-reducing water display system according to claim 15, wherein the irradiation chamber is located in the reservoir.

17. An odor-reducing water display system according to claim 16, wherein the housing is integrally formed with the reservoir.

18. An odor-reducing water display system according to claim 15, wherein the irradiation chamber is located outside of the reservoir.

19. An odor-reducing water display system according to claim 18, wherein a portion of the conduit extends through the housing of the irradiation chamber.

20. An odor-reducing water display system according to claim 19, wherein at least the conduit portion is constructed of one of an ultraviolet transparent and translucent material such that radiant energy from the germicidal light source is transmitted to the liquid through the conduit portion to thereby reduce microbes and their accompanying odor within the conduit.

21. An odor-reducing water display system according to claim 20, wherein the pump is positioned downstream of the irradiation chamber so that microbes are reduced prior to reaching the pump.

22. An odor-reducing water display system according to claim 20, wherein the pump is positioned upstream of the irradiation chamber.

* * * * *